United States Patent [19]
Ross

[11] Patent Number: 4,744,754
[45] Date of Patent: May 17, 1988

[54] DENTAL IMPLANT AND METHOD FOR INSTALLING SAME INTO BONE TISSUE

[75] Inventor: Stanley E. Ross, Boca Raton, Fla.

[73] Assignee: Ross Systems Corporation, Palm Beach, Fla.

[21] Appl. No.: 896,101

[22] Filed: Aug. 13, 1986

[51] Int. Cl.⁴ ............................................. A61C 8/00
[52] U.S. Cl. .................................... 433/173; 433/201.1
[58] Field of Search ............... 433/173, 174, 175, 176, 433/220, 221, 193, 201.1, 210, 213, 214, 223, 195; 264/16, 19

[56] References Cited

U.S. PATENT DOCUMENTS

| | | | |
|---|---|---|---|
| 711,324 | 10/1902 | Lacy | 433/173 |
| 866,304 | 9/1907 | Roach | 433/177 |
| 3,499,222 | 10/1970 | Linkow et al. | 433/174 |
| 3,579,830 | 5/1971 | Morel | 433/174 |
| 3,589,011 | 6/1971 | Sneer | 433/174 |
| 3,729,825 | 5/1973 | Linkow et al. | 433/176 |
| 3,797,113 | 3/1974 | Brainin | 433/173 |
| 3,955,280 | 5/1976 | Sneer | 433/174 |
| 4,065,817 | 1/1978 | Branemark et al. | 3/1.91 |
| 4,180,910 | 1/1980 | Straumann et al. | 433/173 |
| 4,231,120 | 11/1980 | Day | 3/1.91 |
| 4,253,833 | 3/1981 | Edelman | 433/173 |
| 4,304,553 | 12/1981 | Heimke et al. | 433/173 |
| 4,324,550 | 4/1982 | Reuther et al. | 433/174 |
| 4,359,318 | 11/1982 | Gittleman | 433/173 |
| 4,431,416 | 2/1984 | Niznick | 433/174 |
| 4,439,152 | 3/1984 | Small | 433/173 |
| 4,488,875 | 12/1984 | Niznick | 433/173 |
| 4,531,915 | 7/1985 | Tatum, Jr. | 433/173 |

FOREIGN PATENT DOCUMENTS

| | | |
|---|---|---|
| 2516784 | 5/1983 | France ............... 433/201.1 |
| 198909 | 10/1965 | Sweden ............... 433/173 |
| 1291470 | 10/1972 | United Kingdom . |
| 1352188 | 5/1974 | United Kingdom . |
| 1544784 | 4/1979 | United Kingdom . |

OTHER PUBLICATIONS

"A 15-Year Study of Osseointegrated Implants in the Treatment of the Edentulous Jaw", Adell et al., 1981, vol. 10, pp. 387–416.

Primary Examiner—John J. Wilson
Attorney, Agent, or Firm—Burns, Doane, Swecker & Mathis

[57] ABSTRACT

A dental implant is adapted to be installed in a bore formed in jaw bone tissue for retaining a dental prosthesis. The implant comprises a generally cylindrical body defining a longitudinal axis and including an outer periphery. The body is opened at a front end thereof and includes a front cylindrical cavity for receiving a cylindrical bore core. A plurality of through holes is formed in the body and communicates with the front cavity to accommodate the growth of bone tissue therethrough. The body is opened at a rear end thereof and includes a rear cavity communicating with the open rear end for receiving a prosthesis-attachment. The outer periphery of the body can be cylindrically smooth or may include a plurality of longitudinally spaced, circumferentially disposed ribs. There are thus defined on the outer periphery a plurality of circumferentially continuous surface regions adapted to engage the wall of the bore in the bone to resist the flow of blood past the implant. This, in turn, promotes blood clotting and the regeneration and regrowth of bone tissue.

4 Claims, 4 Drawing Sheets

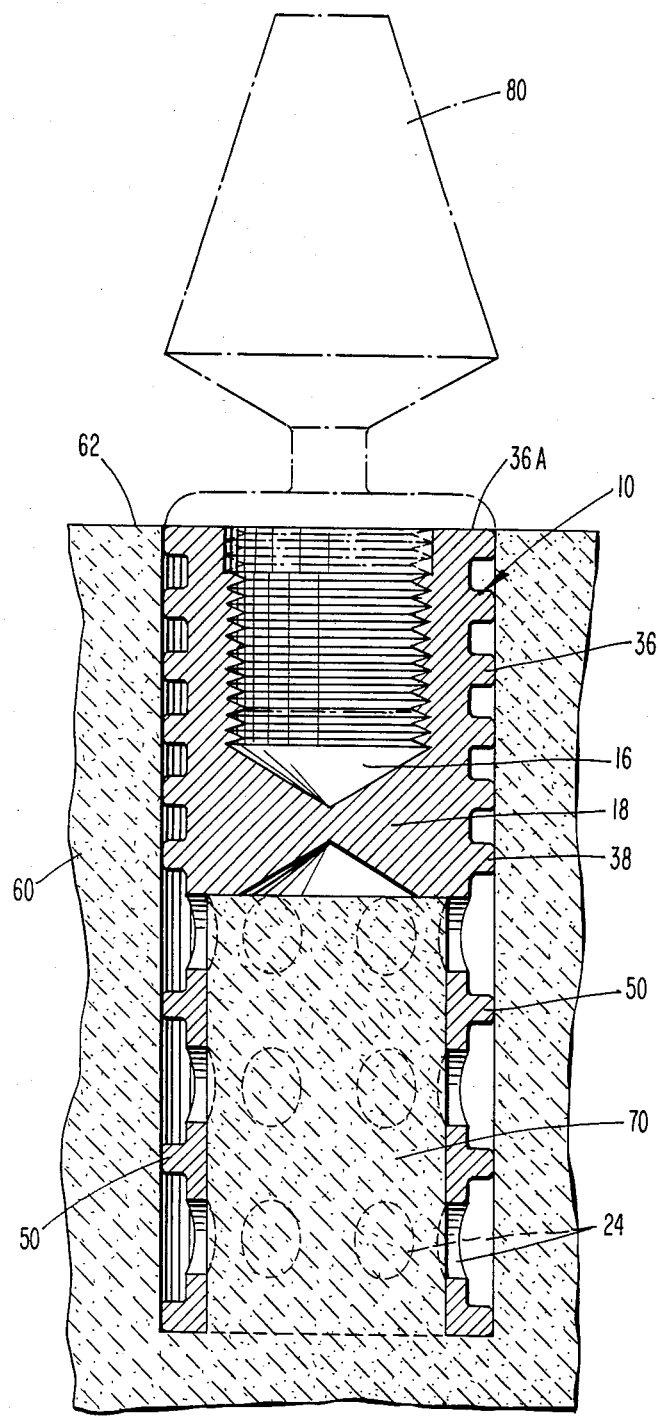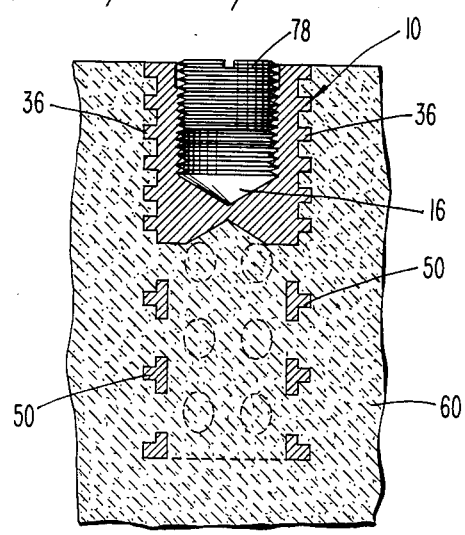

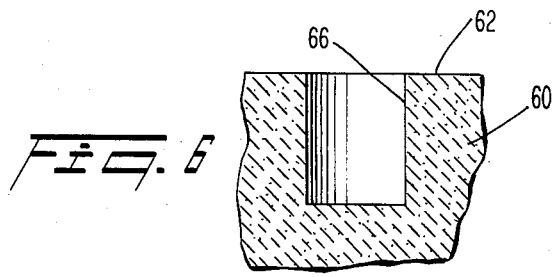
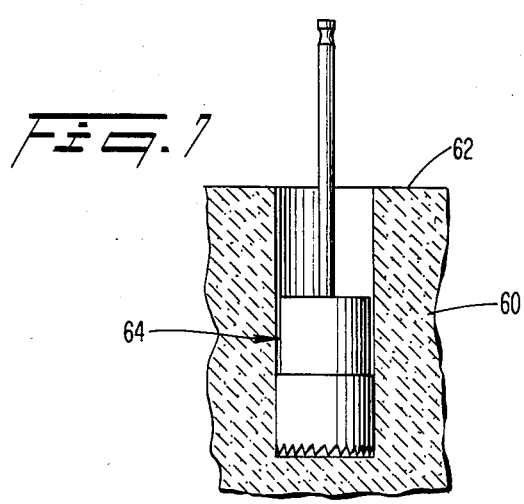
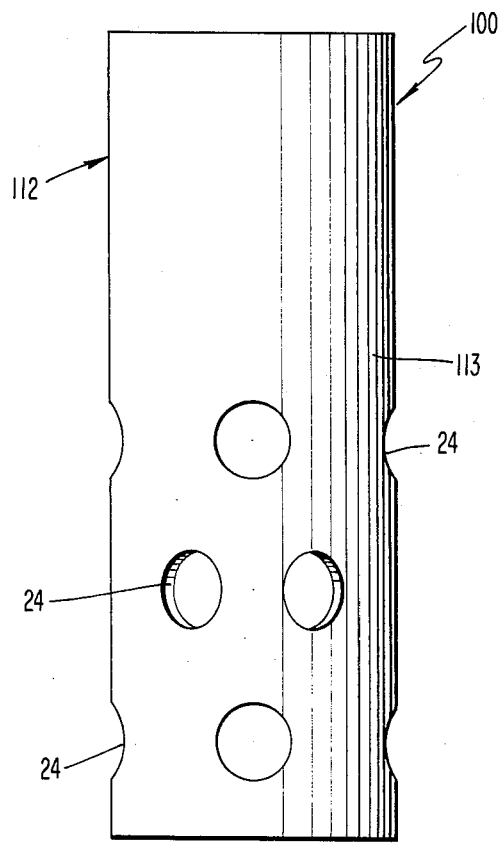
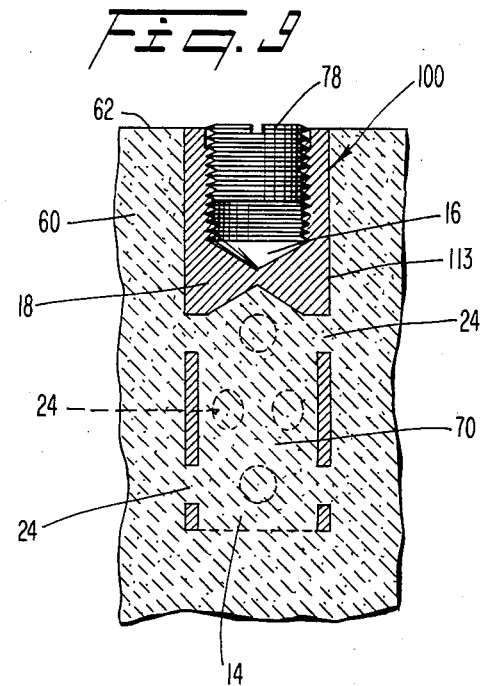
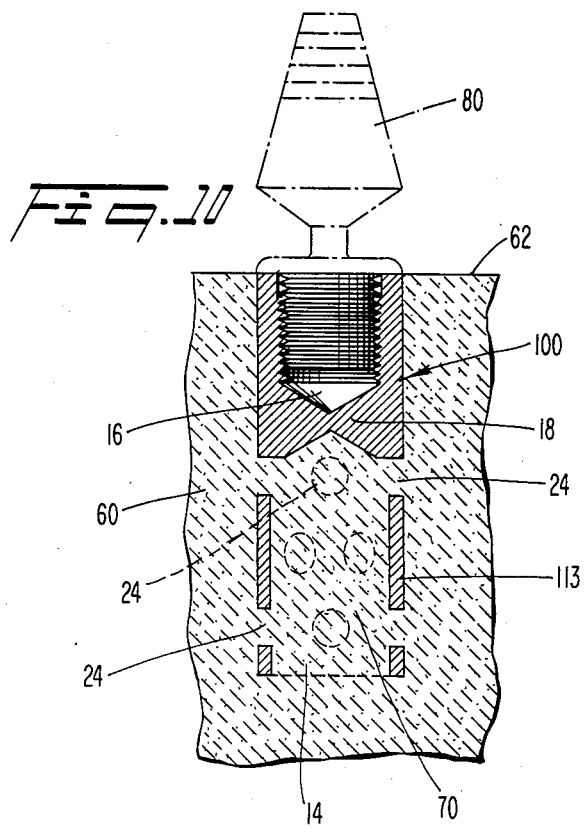

DENTAL IMPLANT AND METHOD FOR INSTALLING SAME INTO BONE TISSUE

RELATED INVENTION

Attention is directed to a related invention of the present inventor disclosed in concurrently filed U.S. application Ser. No. 06/896,524.

BACKGROUND AND OBJECTS OF THE INVENTION

The present invention relates to dental implants which are adapted to be anchored in bone tissue to secure dental prostheses within the mouth. The invention also relates to methods for installing such inserts into bone tissue.

It has been proposed to secure dental prostheses within a patient's mouth by affixing the prostheses to dental implants which are embedded directly within the jaw bone. The implants and embedding techniques heretofore proposed and utilized in practice have not met with universal acceptance among dental practitioners due to considerable limitations regarding the placement of the implants within the mouth and/or uncertainties as to the useful lifespan of the implants.

In that regard, one currently employed technique involves the use of an implant 1 (depicted in FIGS. 11-13 of the accompanying drawings) having external threads 2 by means of which the implant is to be screwed into the bone tissue 3. A bore is first drilled into the bone tissue, the bore having a diameter less than the maximum diameter of the threads of the implant. By screwing the insert 1 into the bore, the threads 2 cut into the bone tissue 3. Variations of such a technique are disclosed in U.S. Pat. Nos. 3,499,222 and 4,431,416 and British Patent Specification No. GB 1,291,470 published Oct. 4, 1972.

However, such a technique can result in so-called "saucerization" wherein some of the bone tissue does not grow back against the implant, i.e., areas between the bone and implant are occupied by soft tissue 4 which does not contribute appreciably to the anchoring of the implant. In cases where implants have been installed in the lower jaw bone, saucerization has been observed to occur at the upper end of the bore. Such saucerized areas can become infected, leading to a spreading of the saucerization along the implant whereby the securement of the implant is significantly undermined.

Although the exact causes of saucerization are not yet known for certain, it is the belief of the present inventor that because of the harsh treatment to which the bone is subjected during implant installation, the rate at which the bone is able to regenerate and grow against the implant is deterred to such an extent that soft gum tissue 4 is able to grow into and occupy the space between the implant 1 and the bone 3 at the open end of the bore. That deterred growth rate may result from a number of factors, including the severe traumatizing of the bone as it is cut and fractured along the region 3A by the self-tapping threads of the implant, and/or the likelihood that the bone is deprived of blood at least at that portion of the bone located at the top of a bore in the lower jaw since blood tends to gravitate away from that bone portion. In that regard, it is well known that blood, once it clots, will develop fibroblasts and osteoblasts which promote the development of bone tissue. By depriving the bone tissue of an ample blood supply, the regeneration and regrowth of bone tissue will be retarded, thereby permitting soft gum tissue to enter the area between the implant and bone. If such saucerization occurs and spreads along the length of the implant, the lifespan of the implant can be significantly shortened.

Some dental practitioners install more than the required number of implants into the bone, whereby the extra implants are kept available as "spares" in the event that the active implant(s) become dislodged from the bone. Besides being more expensive and inconvenient to the patient, that practice is only feasible in cases involving the installation of a relatively long prosthesis wherein the space between the active implant(s) is large enough to accommodate the "spare" implants.

In order to augment the anchoring of the implant, the implant can be provided with a hollow front end which receives a core 5 of the bone (FIG. 12). Such an expedient, disclosed for example in U.S. Pat. Nos. 3,499,222; 4,180,910; 4,359,318; and 4,431,416, involves the cutting of an annular kerf in the bone tissue to leave a cylindrical core of bone surrounded by the kerf. The open front end of the implant receives the core as the implant is inserted into the kerf. The wall of the implant surrounding the core is provided with holes 6 to enable bone tissue to grow through the holes. In the case of implants which include self-tapping screw threads 2, however, the screwing-in of the implant may impose sufficient lateral stresses on the core to cause the core to be broken-off at its base. Even if the core is eventually able to regenerate and regrow, the overall anchoring process could be delayed.

Furthermore, the act of screwing-in a self-tapping implant requires substantial torque imposed by means of a ratchet wrench which mates with a wrench-receiving socket 7 of the implant (FIG. 13). However, such wrenches are relatively large and cumbersome and require a relatively large amount of space to accommodate tool manipulation. Consequently, such implants are not suitable for use in the back portions of a patient's mouth where there exists little room to turn the handle of the wrench, or in narrow areas between existing teeth which are not large enough to accommodate the head of the wrench.

In addition, the fracturing of bone tissue caused by the screw threads renders the implants unsuitable for use in areas of exceptionally thin bone. Therefore, in cases where a patient's bone has been diminished in thickness due to surgical operation, injury, etc., the use of a screw-in type implant may not be feasible.

Therefore, it will be appreciated that for at least the above-discussed reasons, the overall utility and versatility of screw-in type implants has been significantly limited.

It has also been proposed to pre-form female screw threads in the bone by means of a thread-forming drill, rather than by the use of self-tapping threads on the implant. Such a technique is disclosed in an article entitled "A 15-Year Study of Osseointegrated Implants in the Treatment of the Edentulous Jaw" by Adell, Lekholm, Rockler, and Branemark, published in the International Journal of Oral Surgery, Munksgaard, Copenhagen, 1981, Vol. 10, pp. 387-416. In that technique, the thread-forming drill does not leave a core in the bore to augment the anchoring action. Also, the drill is designed to form a widening at the mouth of the bore to accommodate the insertion of an implant having an enlarged collar at is outer end. In practice, saucerization results from the formation of such an widening, and the saucerization gradually spreads, e.g., by about 0.10 mm per year along the length of the implant according to the above-referenced article. Once a sufficient length of saucerization has occurred, the implant will be inadequately anchored. It should further be noted that even though the female threads are predrilled in the bore, the threads on the implant are intended to be partly self-tapping. Thus, a wrench is needed, whereby the areas of the mouth in which that implant can be employed are limited, and a certain amount of bone fracture and bone trauma will likely occur during installation of the implant.

It is, therefore, an object of the present invention to minimize or obviate problems of the types discussed above.

A further object is to provide dental implants and methods for installation thereof which minimize bone fracturing and traumatization and resist the occurrence of saucerization.

Another object is to provide such methods and apparatus which promote the regeneration and regrowth of surrounding bone tissue.

A further object is to provide such methods and apparatus which enable the implant to be installed in confined and narrow areas of the mouth and in thin bone tissue.

Yet another object is to enable an implant to be installed without the need for cement or wrenches.

An additional object is to promote the retention of blood and blood clots adjacent the cut bone tissue to promote the regeneration and growth of that bone tissue.

Still another object is to provide a hollow implant which fits over a bone core and which can be installed without an appreciable risk of breaking the core.

SUMMARY OF THE INVENTION

These objects are acheived by the present invention which relates to a dental implant adapted to be installed into a predrilled bore formed in a jaw bone tissue for retaining a dental prothesis. The implant comprises a generally cylindrical body defining a longitudinal axis. The body is open at a front end thereof and includes a front cylindrical cavity communicating with the open front end for receiving a cylindrical bone core. The front cavity is surrounded by a front portion of the body. That front portion is apertured to accommodate the growth of bone tissue therethrough. The body is opened at a rear end. The rear cavity has internal screw threads for receiving an externally threaded prothesis-attachment. The rear cavity is surrounded by a rear portion of the body, wich rear portion is non-apertured. The front and rear portions of the body include front and rear outer peripheries, respectively, which are of the same diameter and define a maximum outer diameter of the implant.

Preferably, the rear outer periphery includes surface regions which are circumferentially continuous and longitudinally extending to resist the passage of blood longitudinally therepast. In one preferred embodiment, the rear outer periphery is of uniform diameter to define an infinite number of those circumferentially continuous surface regions. In another preferred embodiment, the rear outer periphery includes circumferentially extending grooves disposed in longitudinally alternating relationship with said circumferentially continuous surface regions.

The invention also pertains to a method of installing an implant wherein the front cavity frictionally receives a bone core, and the outer periphery of the implant frictionally engages an inner wall of the bore in the bone to resist the flow of blood therepast to promote the clotting of blood and thus promote the regeneration and regrowth of bone tissue.

BRIEF DESCRIPTION OF THE DRAWINGS

The objects and advantages of the invention will become apparent from the following detailed description of a preferred embodiment thereof in connection with the accompanying drawings in which like numerals designate like elements, and in which:

FIG. 3 is a view similar to FIG. 2 after the implant has been pushed into the predrilled bore;

FIG. 4 is a view similar to FIG. 3 with a prosthesis attachment threadedly mounted in the implant;

FIG. 5 is a view similar to FIG. 3 with a retaining screw threadedly mounted in the implant;

FIGS. 6 and 7 are schematic views representing steps involved in installing the implant in bone tissue;

FIG. 8 is a side elevational view of a second embodiment of a dental implant according to the present invention;

FIG. 9 is a longitudinal sectional view taken through the implant of FIG. 8;

FIG. 10 is a view similar to FIG. 9 after the implant has been pushed into a pre-drilled bore, and a prosthesis attachment is depicted in broken lines;

DETAILED DESCRIPTION OF A PREFERRED EMBODIMENT OF THE INVENTION

Figure 1:
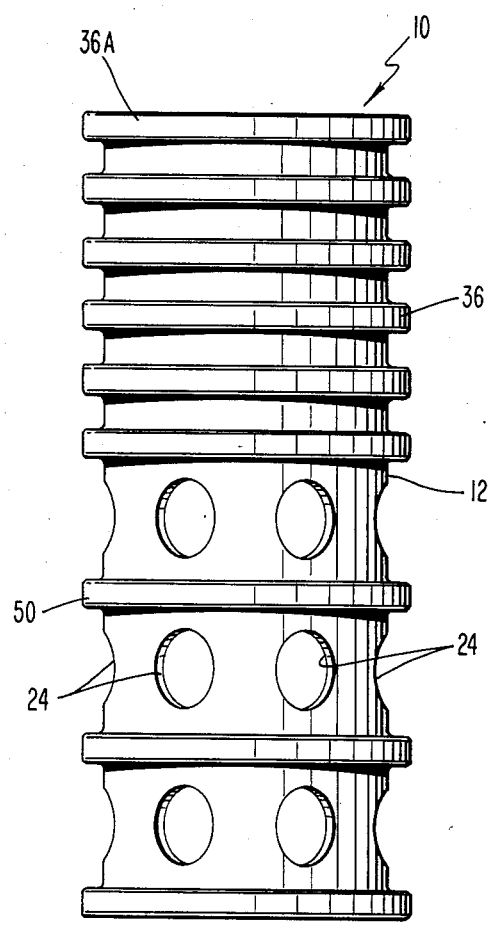
FIG. 1 is a side elevational view of a first embodiment of a dental implant according to the present invention.
Figure 2:
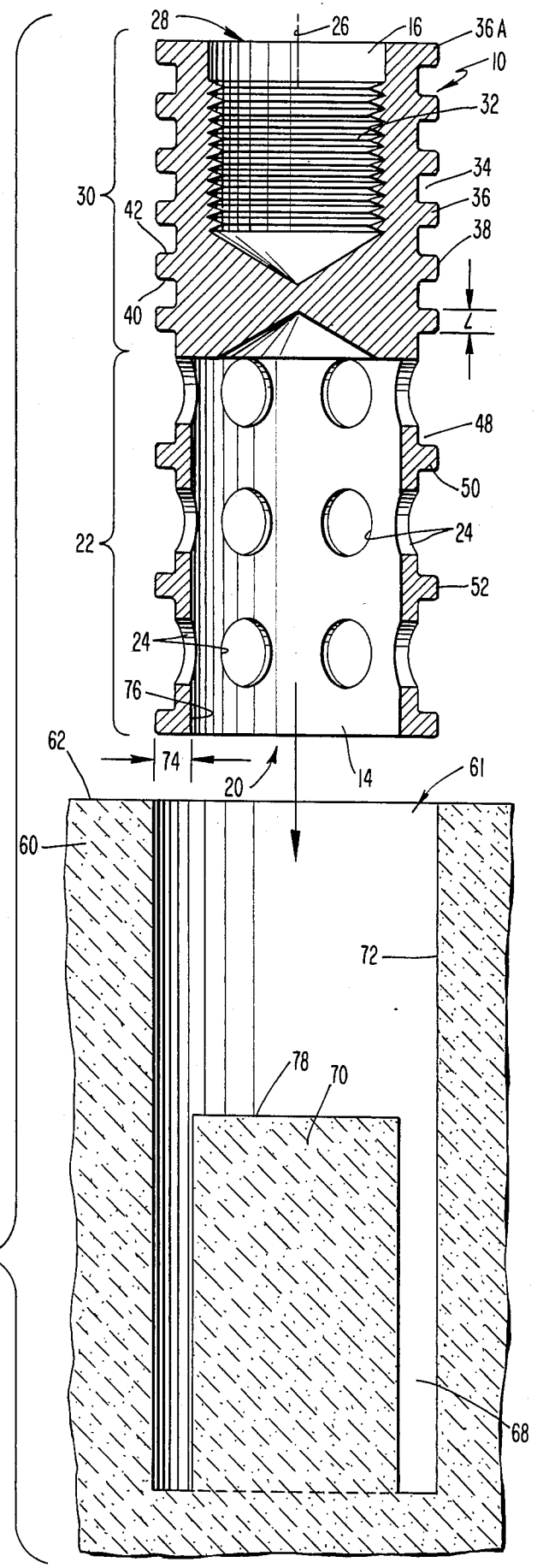
FIG. 2 is a longitudinal sectional view taken through the implant of FIG. 1 as the implant is being advanced toward a predrilled bore in bone tissue.
Figure 11:
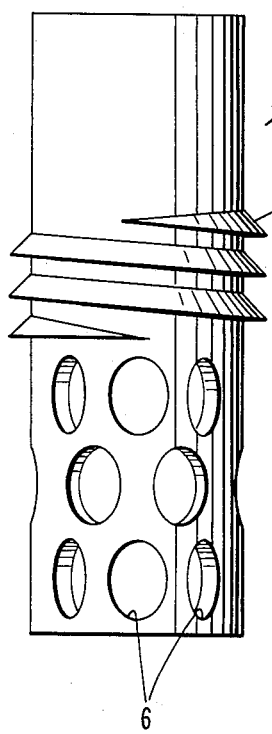
FIG. 11 is a side elevational view of a prior art implant.

A dental implant 10 according to the present invention, depicted in FIGS. 1–8, is suitable for use in lower jaw bones. The implant comprises a generally cylindrical body 12 formed of a biocompatable material such as, for example, titanium such as commercially pure titanium or a titanium alloy such as Ti 6AL 4V, or other equivalent materials as will be apparent to those skilled in the art. The body defines front and rear circular cylindrical cavities 14, 16 which are separated by a divider wall 18 (FIG. 2). The front cavity 14 is open toward a front end 20 of the body 12 and is surrounded by a front portion 22 of the body. That front portion 22 is apertured by means of a plurality of through-holes 24. The through-holes are arranged in circumferential rows, each row being spaced apart in a direction parallel to the longitudinal axis 26 of the body.

The rear cavity 16 opens toward a rear end 28 of the body 12 and is surrounded by a rear portion 30 of the body. That rear portion 30 is non-apertured, i.e., it does not afford any appreciable external communication for the rear cavity except via the rear opening 28. The rear cavity includes an internal wall which contains female screw threads 32.

The exterior of the rear portion 30 comprises a plurality of longitudinally alternating grooves 34 and ribs 36.

The ribs 36 are circular and extend circumferentially continuously around the body 12 in a plane oriented perpendicularly relative to the axis 26. Each rib includes an outer surface 38 which is smooth and extends circumferentially continuously. That is, the surface 38 is circular as opposed to being helical as in the case of screw threads. The surface 38 also has a dimension L in the longitudinal direction. The surface 38 is flat in the longitudinal direction although the front and rear edges of the surface are slightly radiused to eliminate sharp corners. The outer surfaces 38 are of equal outer diameter and define the outer periphery of the rear portion 30.

Each rib lies in a plane extending transversely to the axis 26 and includes front-facing and rear-facing surfaces 40, 42 which are circumferentially continuous and oriented perpendicularly relative to the axis 26. Accordingly, the rearwardly facing surfaces 42 extend outwardly in a direction no portion of which extends forwardly.

The exterior of the front portion 22 of the body 12 includes longitudinally alternating grooves 48 and ribs 50. The through-holes 24 are formed in the bases of the grooves 48. Each rib 50 is shaped similarly to the ribs 36, e.g., each rib 50 includes an outer peripheral surface 52 which is smooth and which extends circumferentially continuously and also longitudinally. The diameter of the outer surface 52 is equal to that of the outer surfaces 38 of the ribs 36 on the rear portion 30. It will thus be appreciated that the outer surfaces 52, 38 define the outer peripheries of the front and rear portions 22, 30, respectively, as well as the maximum outer diameter of the implant.

The implant is installed in accordance with the following procedure. The gum tissue overlying the area of the jaw bone 60 of either the upper or lower jaw in which the implant is to be affixed is cut and folded back to expose the bone surface 62. A circular cylindrical bore 61 is then formed in the bone. This can be performed in stages in accordance with a conventional technique wherein a trephine drill 64 cuts a circular kerf in the bone to form an expendable core of bone. That expendable core of bone is removed to leave a cylindrical hole 66 as depicted in FIG. 6. The drill 64 is then further advanced into the bone (FIG. 7) to create an additional kerf 68 (FIG. 2) which, in turn, defines a circular cylindrical permanent core 70. The bore now contains a circular cylindrical inner wall 72 of uniform diameter from the bone surface 62 to the base of the kerf 68. The drill size is selected such that the diameter of the wall 72 corresponds to the diameter of the outer surfaces 38, 52 of the ribs 36, 50, and such that the radial thickness of the kerf 68 corresponds to the radial thickness 74 (FIG. 2) of the front portion 22, i.e., the distance from an inner wall 76 of the front cavity to the outer surfaces 52 of the ribs 50. Thus, the outer diameter of the permanent core 70 corresponds to the diameter of the inner wall 76 of the front cavity.

In addition, the longitudinal distance from the end face 78 of the core 70 to the jaw bone surface 62 is equal to the sum of the longitudinal thickness of the divider wall 18 and the longitudinal dimension of the rear cavity 16. Furthermore, the longitudinal dimension of the kerf 68 is at least equal to that of the front cavity 14.

The implant is installed by being pushed, front end first, into the bore 61. Due to the above-described dimensional relationships, the outer periphery of the body, as defined by the outer surfaces 38, 52 of the ribs, will slide frictionally along the inner wall 72 of the bore, and the front cavity 14 will telescopingly receive the core 70 as the inner wall 76 of the front cavity slides frictionally along the outer peripheral surface of the core.

Therefore, once pushed-in, the implant will be snugly held within the bore (FIG. 3). This is achieved without cracking or traumatizing the bone and without breaking the core 70. Hence, no undue delays in the initiation of bone regrowth will occur. Furthermore, since the circumferentially uninterrupted outer surfaces 38, 52 press against the wall 72 of the bore or at least are in extremely close proximity to the wall 72, the tendency for blood to gravitate along the wall 72 will be resisted, thereby promoting the formation of blood clots in the immediate vicinity of the bone tissue. The formation of blood clots leads to the development of the necessary cells for bone formation, such as fibroblasts and osteoblasts. As a reuslt, the regeneration and regrowth of bone tissue is promoted. Thus, it is assured that such bone regrowth will not only occur, but will occur rapidly without undue delay. Accordingly, the healing process will be accelerated.

Figure 12:
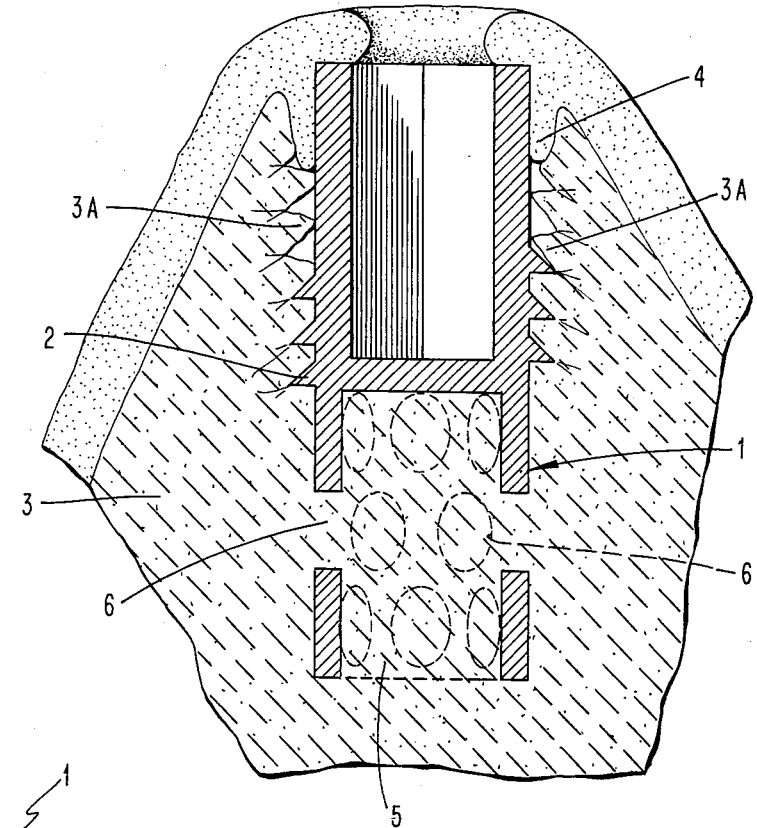
FIG. 12 is a cross-sectional view of the FIG. 12 implant after it has been screwed into a jaw bone.
Figure 13:
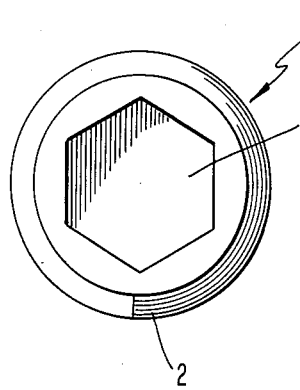
FIG. 13 is a top view of the FIG. 12 implant.

As noted earlier herein, the lack of blood available to bone tissue may not only retard bone regrowth, but may even result in an absence of bone regrowth in the blood-deprived areas. One such area, for example depicted at 4 in FIG. 12, is situated at the mouth of a bore formed in the lower jaw bone since blood will flow from that area gravitationally. However, the presence of blood clots adjacent the rear portion of the implant eliminates the possibility that the bone tissue near the mouth of the bore will be deprived of blood. Furthermore, since the bone is not fractured by the implant (in contrast to implants employing self-tapping threads), the implant will be in contact with healthy bone and thus will be capable of resisting dislodgment of the implant. Also, no spaces will be created into which soft tissue may grow. The rearwardmost rib 36A is situated at the rearmost end of the implant and aids in closing-off the mouth of the bore.

Very quickly, then, the bone tissue located externally around the implant and internally within in the front cavity 14 will grow toward the implant and become adhered thereto (i.e., adherence occurs since the implant is formed of a biocompatable material). Bone tissue will also grow into the grooves 34, 48 between the ribs 36, 50 and through the through-holes 24 to strongly resist dislodgement of the implant.

At the time when the implant is pushed into the bore 61, the rear cavity preferably contains a threaded-in retaining pin 78 (also formed of the afore-described biocompatible material) to prevent the entry of foreign matter into the rear cavity (see FIG. 5). After the healing process has progressed sufficiently, the retaining pin can be removed and replaced by a threaded insert 80 (depicted in in FIG. 4) to which a dental prosthesis (not shown) may be attached. Thus, the implant and insert 80 are both installed without the use of cement.

Since there is no need to screw-in the implant via self-tapping screw threads, there is no need to employ a wrench. Hence, the implant can be easily installed in all areas of the mouth. Also, the implant can be inserted into any space which is large enough to receive a single tooth, i.e., the implant is not restricted to use only in spaces large enough to accommodate the head of a wrench.

Another preferred embodiment of the invention depicted in FIGS. 8 to 10, involves an implant 100 which is similar in construction and materials to that disclosed in connection with FIGS. 1 to 3 except that the outer periphery of the body 112 is defined by a smooth cylindrical surface 113 rather than by alternating ribs and grooves. The implant 100 is installed in the manner disclosed earlier in connection with FIGS. 2, 6 and 7. It will be appreciated that whereas the earlier described implant 10 involves only a limited number of circumferentially continuous regions (defined by the outer surfaces 38, 52) which frictionally engage the inner wall 72 of the bone, the implant 100 contains an infinite number of such circumferentially continuous regions which frictinally engage the wall 72. Thus, the entire outer periphery 113 of the implant 112 will be available for frictional engagement with the wall 72 of the bone to resist blood flow and thereby promote the clotting of blood. Accordingly, the advantages described earlier herein with reference to the implant 10 of FIGS. 1-3 are applicable as well to the implant 100 of FIGS. 8 to 10.

Although the present invention has been described in connection with a preferred embodiment thereof, it will be appreciated by those skilled in the art that modifications, additions, substitutions, and deletions not specifically described may be made without departing from the spirit and scope of the invention as defined in the appended claims.

What I claim is:

1. A dental implant adapted to be installed in a pre-drilled bore formed in jaw bone tissue for retaining a dental prosthesis, said implant comprising a generally cylindrical body defining a longitudinal axis, said body being open at a front end thereof and including a cylindrical front cavity communicating with said open front end for receiving a cylindrical bone core, said front cavity being surrounded by a front portion of said body, said front portion including a plurality of circumferentially and radially spaced through-holes extending radially completely therethrough to accommodate the growth of bone tissue therethrough, said body being open at a rear end thereof and including an internally threaded cylindrical rear cavity which communicates with said open rear end and adapts said rear cavity to receive externally threaded prosthesis-attachment means, said rear cavity being surrounded by a rear portion of said body, said rear portion being non-apertured, said front and rear portions of said body including front and rear outer peripheries, respectively, each of said front and rear outer peripheries including a plurality of longitudinally spaced, circumferentially extending ribs, each rib lying in a plane extending transversely to said longitudinal axis, at least some of said ribs on said front outer periphery being disposed longitudinally between longitudinally spaced ones of said through-holes, said ribs on said front and rear outer peripheries including outer surfaces which are of the same diameter and define a maximum outer diameter of said implant.

2. A dental implant according to claim 1, wherein said outer surfaces are circumferentially endless and longitudinally extending to resist the passage of blood longitudinally therepast.

3. A dental implant according to claim 1, wherein said ribs include longitudinally rearwardly facing surfaces extending outwardly in a direction of which no portion extends forwardly.

4. A method of installing a dental implant in a jaw bone, said implant being of the type comprising a generally cylindrical body defining a longitudinal axis, said body being open at a front end thereof and including a cylindrical front cavity communicating with said open front end for receiving a cylindrical bone core, said front cavity being surrounded by a front portion of said body, said front portion being apertured to accommodate the growth of bone tissue therethrough, said body being open at a rear end thereof and including a cylindrical rear cavity which communicates with said open rear end and adapts said rear cavity to receive externally threaded prosthesis-attachment means, said rear cavity being surrounded by a rear portion of said body, said rear portion being non-apertured, said front and rear portions of said body including front and rear outer peripheries, respectively, which are of the same diameter and define a maximum outer diameter of said implant, said method comprising the steps of:

drilling a closed-ended bore in a jaw bone such that said bore includes an inner cylindrical wall of uniform diameter extending forwardly from a surface of said bone to a closed front end of said bore, and a cylindrical core extending rearwardly from said closed end, said core including an outer peripheral surface coaxial with said inner wall and spaced radially inwardly therefrom to define an annular kerf having a radial dimension substantially equal to a radial thickness of said front portion of said body, said outer peripheral surface of said core defining a diameter substantially equal to a diameter of said front cavity of said implant, pushing said implant into said bore such that said outer peripheries of said front and rear portions of said body frictionally slide against said inner wall of said bore without penetrating said inner wall, and an inner wall of said front cavity frictionally slides against said outer wall of said core as said core enters said front cavity, and terminating the insertion of said implant such that said inner wall of said front cavity frictionally engages said outer peripheral surface of said core, and said front and rear outer peripheries of said body frictionally engage said inner wall of said bore in a circumferentially uninterrupted manner to resist the travel of blood therepast.

* * * * *